United States Patent [19]
Hazenbos

[11] Patent Number: 6,082,531
[45] Date of Patent: Jul. 4, 2000

[54] DEVICE AND METHOD FOR DISPLAYING DECIDUOUS TEETH AND MOLARS

[75] Inventor: Bartholomeus Franciscus Wilhelmus Hazenbos, Milsbeek, Netherlands

[73] Assignee: Bartholomeus Franciscus W. Hazenbos, Milsbeek, Netherlands

[21] Appl. No.: 09/199,097

[22] Filed: Nov. 24, 1998

[30] Foreign Application Priority Data

Nov. 25, 1997 [NL] Netherlands ............................ 1007610
Aug. 13, 1998 [NL] Netherlands ............................ 1009859

[51] Int. Cl.⁷ .............................. A61C 19/10; A61B 19/02
[52] U.S. Cl. ................................ 206/83; 206/63.5; 433/26
[58] Field of Search ............................ 206/63.5, 83, 232; 433/26, 229

[56] References Cited

U.S. PATENT DOCUMENTS

| | | | |
|---|---|---|---|
| 2,302,376 | 11/1942 | Myerson | 433/26 |
| 2,334,214 | 11/1943 | Myerson | 433/26 |
| 2,412,352 | 12/1946 | Myerson | 433/26 |
| 2,705,815 | 4/1955 | Braver | 433/196 X |
| 3,018,884 | 1/1962 | Fritz | 206/83 |
| 3,111,760 | 11/1963 | Semmelman et al. | 433/26 |
| 4,775,318 | 10/1988 | Breslin | 433/26 |
| 4,923,058 | 5/1990 | Dennison | 206/83 |
| 5,289,915 | 3/1994 | Queen | 206/38 |
| 5,303,819 | 4/1994 | Goldberg | 206/83 |
| 5,553,702 | 9/1996 | Walsh | 206/232 X |
| 5,621,990 | 4/1997 | Blenchard | 206/83 X |
| 5,904,481 | 5/1999 | Shima | 433/26 |

*Primary Examiner*—Bryon P. Gehman
*Attorney, Agent, or Firm*—Hoffman & Baron, LLP

[57] ABSTRACT

Device and method for displaying lost teeth and molars, in particular tooth and molars of the human deciduous dentition. The device comprises at least one holder member having a deformable portion in which the lost teeth and/or molars can be pressed, the thus obtained attachment being a prolonged attachment.

19 Claims, 8 Drawing Sheets

DEVICE AND METHOD FOR DISPLAYING DECIDUOUS TEETH AND MOLARS

This invention relates to a device for displaying teeth and molars of the human deciduous dentition.

Such a device is known from U.S. Pat. No. 4,694,956. The drawback of the known device is that it is very costly. This is caused in particular by the fact that the tooth/molar receiving means are designed as a number of compartments which are suitable for receiving a single tooth or molar and which are hingedly connected to a first or second holder member. The manufacture of the two holder members and the separate compartments, and the mounting of these compartments onto the two holder members lead to a very costly device. Owing to its cost price, the known device has never become a commercial success. Further, placing the deciduous teeth and molars in the compartments is rather cumbersome and is some cases it is impossible to place a tooth or molar in the compartment associated with that tooth or molar because the tooth or molar in question is too large.

The object of the invention is to provide a device of the type described in the opening paragraph hereof without the above-mentioned disadvantages, which device moreover, is suitable for the prolonged retention of the deciduous teeth and molars, without this necessitating any particular aftertreatment of the device.

To that end, according to the invention, the device of the type described in the preamble is characterised in that the tooth/molar receiving means are designed as a deformable portion into which the deciduous teeth and/or molars can be pressed, such that the attachment thereby obtained is a prolonged attachment.

The device is relatively inexpensive because it consists of only a small number of parts, and it undergoes only few assembly operations before it can be put into use. Since the attachment is a prolonged attachment, the device does not need to undergo any costly aftertreatment after all teeth and molars have been collected. 'A prolonged attachment' is herein to be understood to mean an attachment over a period of at least about 5 years. The deformable portion can be designed, for instance, as an elastically deformable clamping groove in the at least one holder member.

According to a further elaboration of the invention, however, it is preferred for the deformable portion to be designed as a substance which, at least under certain conditions, is plastic.

It is noted that it known per se from U.S. Pat. No. 2,705,815 to use a plastic substance in the form of a thin layer of beeswax for temporary adhesion of the fallen-off teeth and molars. The holder comprises for each tooth or molar a recess in which a thin layer of beeswax is provided. Owing to the presence of the separate recesses, the teeth and molars, in particular when they are small, will be spaced apart. From an aesthetic point of view, this is particularly unfavorable. Moreover, a disadvantages of beeswax is that it has a relatively low melting point (about 63° C.) and already softens at much lower temperatures to the extent where it loses its adhesive power. When the known holder is placed on a sunny window-sill, it is undoubtedly possible that the beeswax melts and the tooth fall from the holder. In fact, for prolonged retention, this publication proposes an aftertreatment for which the device is to be sent to a laboratory. In this aftertreatment, the beeswax is removed and the teeth and molars are embedded by the laboratory worker in hard plastic, preferably of the same kind as the plastic of which the holder is made. This publication therefore teaches the person of ordinary skill in the art away from the use of plastic substance for prolonged retention. It is clearly stated that is desirable that for the purpose of prolonged retention, the tacky wax layer be removed and replaced by a bond forming an integral part of the holder. To that end, according to the document, "it will undoubtedly be necessary to have the form sent into a central laboratory for completion". It is self-evident that this entails such high costs that the average private individual will not proceed to purchase the known holder.

According to a further elaboration of the invention, it is particularly favorable when the at least one holder member is provided with at least one recess in which the plastic substance is received, the dimensions of the at least one recess being such, and the amount of plastic substance received in the at least one recess being such, that the root or the residual portion of the side of the tooth or molar remote from the crown, in the mounted condition of the tooth or molar, is substantially completely embedded in the plastic substance, so that a prolonged retention of the tooth or molar in the plastic substance is ensured.

The plastic substance is present in a strand or layer of such thickness and/or depth that teeth and molars of different dimensions can be pressed into it, with the root or the residual portions of the root being fully embedded in the plastic substance. This is in contrast to U.S. Pat. No. 2,705,815, where no embedding is involved but where the beeswax is applied in a very thin layer to which the teeth or molars are adhered.

Placing the teeth and molars in the plastic substance for prolonged retention is simple and can be done by a parent or even by the child itself. Moreover, a tooth or a molar of any dimension can be embedded in the substance.

According to a further elaboration, it is preferred for the device to comprise a first, continuous, groove-shaped recess for receiving the upper teeth and upper molars, and a second, continuous, groove-shaped recess for receiving the lower teeth and lower molars.

According to an alternative further elaboration of the invention, the device can also be provided with a single, continuous, groove-shaped recess for receiving both the upper teeth and molars and the lower teeth and molars.

The groove-shaped recesses have the advantage over separate recesses for each tooth or molar, that the teeth and molars can be embedded in the plastic substance so as to be arranged one against the other. This renders the device suitable for esthetically accommodating therein both large and small milk teeth and molars.

According to a further elaboration of the invention, the plastic substance can be a plastic, such as, for instance, a cement or synthetic resin, which is plastic at room temperature and which retains these properties for a prolonged period of time. Such plastic substances, such as, for instance, silicone rubber, are known per se. Preferably, the plastic substance continues to exhibit substantially the same plasticity up to a temperature of at least about 65° C. Even on a hot window-sill, the prolonged retention of the teeth and molars then remains guaranteed.

According to an alternative further elaboration of the invention, the plastic substance can be a thermoplastic plastic which is hard at room temperature and is plastic at a temperature of more than at least about 30° C. To place a tooth or molar in such a plastic, it is necessary, prior to placing the tooth or molar, to heat the plastic, using, for instance, an electric hair-drier. As soon as the plastic has become plastic under the influence of the heat of the hair-drier, the tooth or molar can be pressed into the plastic, whereafter the plastic will cure again after some time, so that the tooth or molar is fixedly bonded to the cured thermoplastic plastic.

The invention further relates to a method for storing the teeth and molars from a human deciduous dentition in a molar member, the holder member comprising at least one groove-shaped recess in which, for accommodating therein the teeth and molars from the upper jaw and/or lower jaw, a plastic substance is provided, the dimensions of the at least one groove-shaped recess and the amount of plastic substance provided therein being such that upon pressing a fallen-off tooth or molar therein, a root or a residual portion of the side of the tooth or molar remote from the crown is substantially completely embedded in the plastic substance, so that a prolonged retention of the tooth or molar in the plastic substance is ensured.

According to a further elaboration of the method, it is then particularly favorable when, for the purpose of the plastic substance, a plastic is used, such as, for instance, a plastic cement or synthetic resin, which plastic is plastic at room temperature and which retains these plastic properties for a prolonged period. 'A prolonged period' is herein understood to mean a period of at least about 5 years. A period of about 10 years or more is preferred.

Optionally, after all teeth and molars have been placed in the holder member, a curing agent can be applied to the plastically deformable plastic, such that the plastic substance cures and the attachment of the teeth and molars changes from a detachable prolonged attachment to a fixed prolonged attachment. In that way, unauthorized removal of teeth or molars form the set can be prevented.

Further elaborations of the invention are described in the subclaims and will be further clarified on the basis of two exemplary embodiments, with reference to the drawing.

Figure 1:
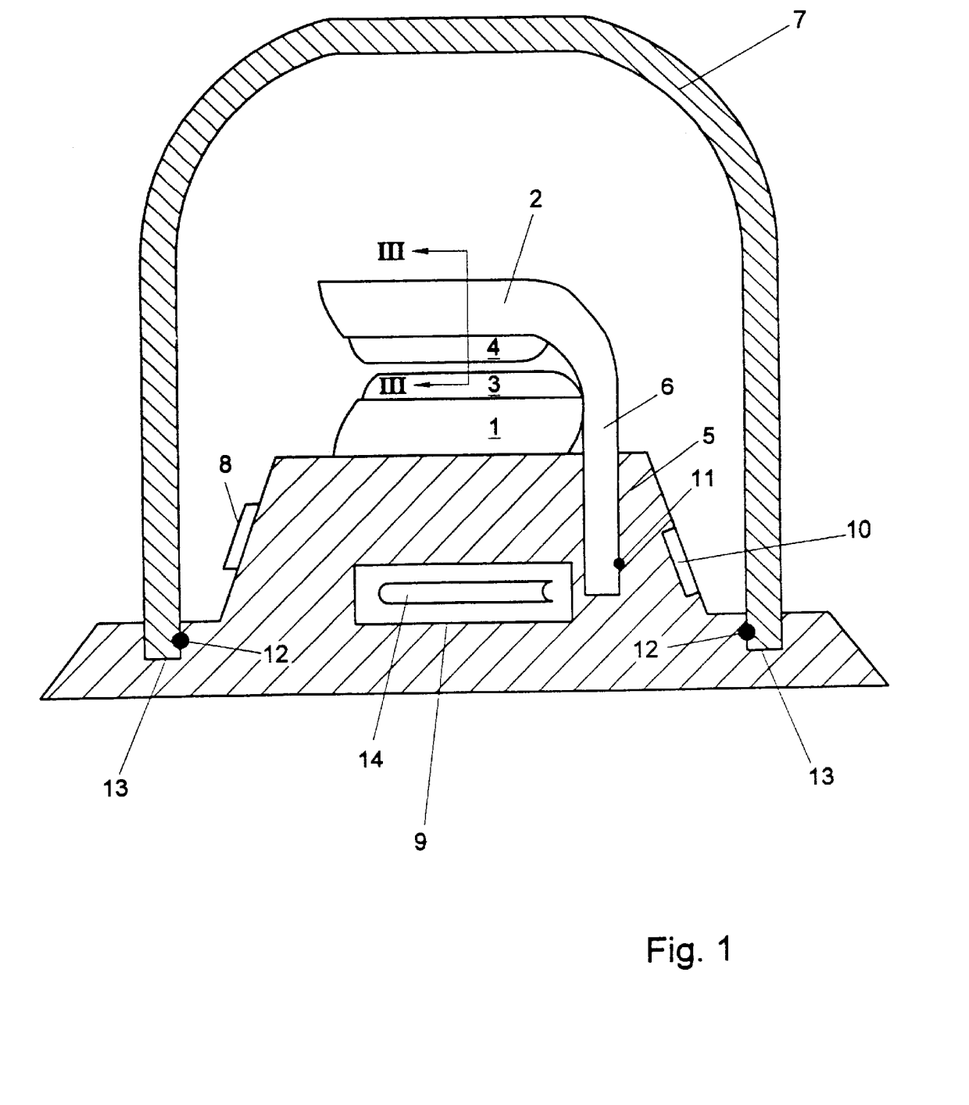
FIG. 1 shows a side elevation of a first exemplary embodiment of the device according to the invention.
Figure 2:
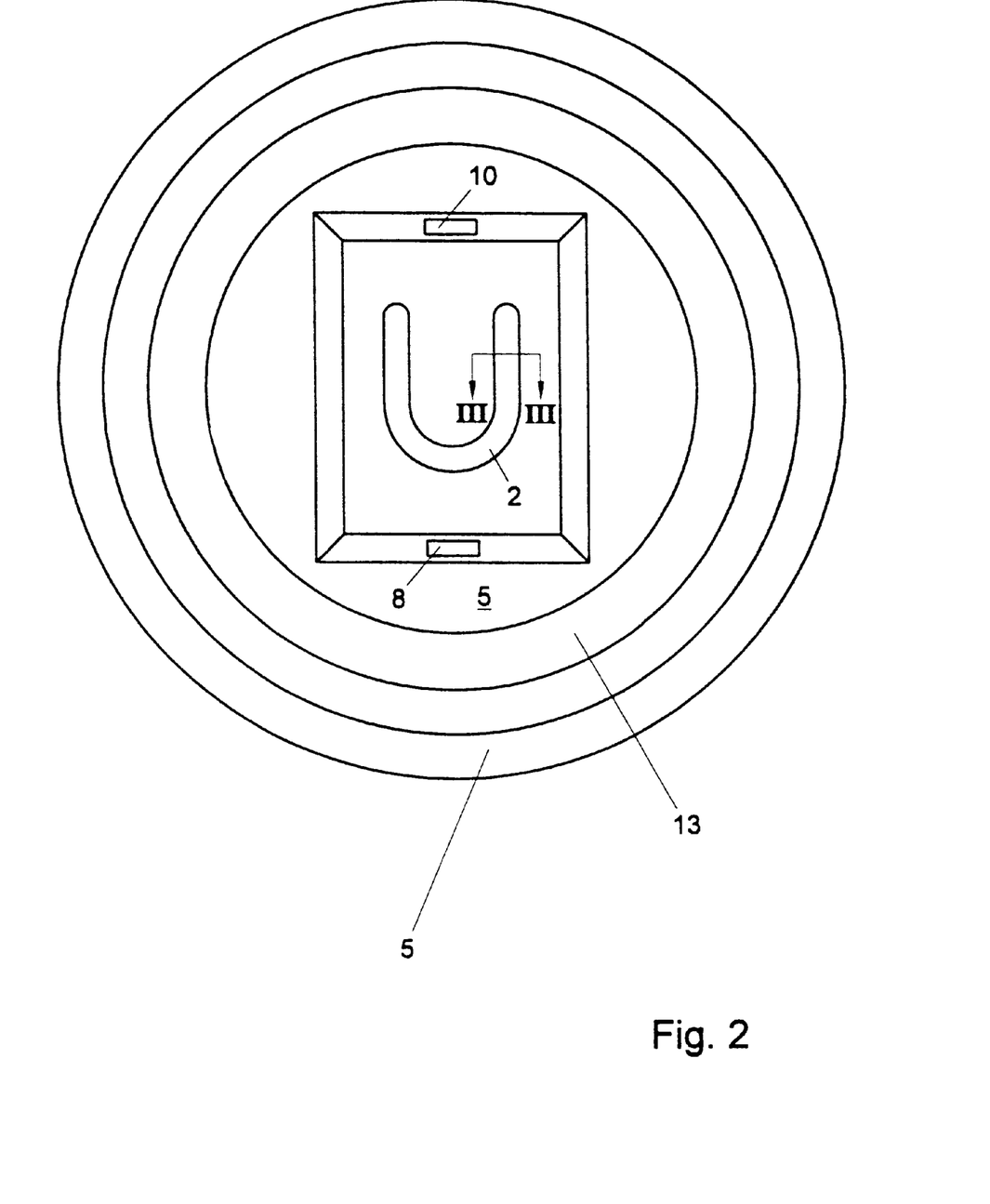
FIG. 2 shows a top plan view of the exemplary embodiment represented in FIG. 1.
Figure 3:
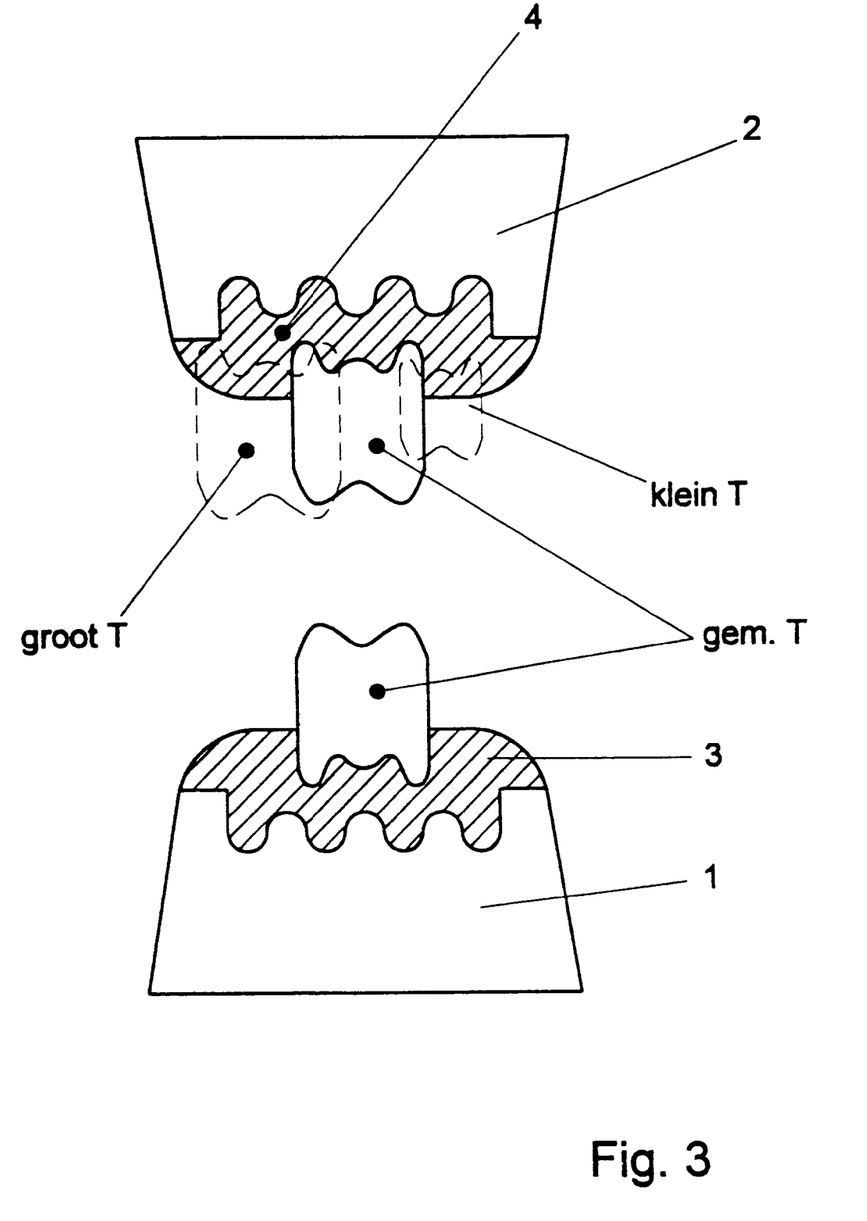
FIG. 3 shows a cross-sectional view taken on the line III—III in FIGS. 1 and 2.

The exemplary embodiment of the device as shown in FIGS. 1–3 for displaying lost teeth and molars, in particular teeth and molars of the human deciduous dentition, comprises a first holder member 1 serving as lower jaw, which is mounted on a pedestal 5. Optionally, the first holder member 1 can be an integral part of the pedestal 5 and be designed as a single injection molded part. The device further comprises a second holder member 2, serving as upper jaw. The second holder member 2 is provided with a support 6 which is detachably connected to the pedestal 5. Both the first and the second holder member 1 and 2, respectively, are of substantially U shaped design, which is clearly visible in FIG. 2. The facing sides of the first holder member 1 and the second holder member 2 are provided with a substance 3 and 4, respectively, which is plastic at least under certain conditions, into which substance the lost teeth and/or molars T can be pressed.

The plastic substance 3, 4 can be a plastic, such as, for instance, a cement or synthetic resin, such as, for instance, silicone rubber, which is plastic at room temperature. Optionally, directly before or after placing a tooth or molar, a curing component can be applied locally, so that the plastic substance cures at the point and a fixed bonding of the tooth or molar is effected. It is also possible, however, that the plastic substance 3, 4 is a thermoplastic plastic which is hard at room temperature and is plastic at a temperature of more than at least about 30° C. In the latter case, before a tooth or molar T can be pressed into the plastic substance, the thermoplastic plastic must be heated so as to render it plastic. After cooling, the thermoplastic plastic cures again, with the tooth or molar T fixedly bonded to the thermoplastic plastic.

In FIG. 3, it is clear to see how the plastic substance 3, 4 is connected with the associated holder members 1 and 2, respectively. It is also clearly indicated how a tooth T has been pressed into the substance, that is, such that the root or the residual portion of the side of the tooth or molar remote from the crown is substantially completely embedded in the plastic. Applying a broad strip or strand of plastic substance 3, 4 creates the possibility of placing teeth and/or molars T more towards the inner edge or more towards the outer edge of the holder members 1, 2, so that sets of teeth both large and small can be displayed in the device. These inner and outer positions are represented in dotted lines in the second holder member 2.

In the exemplary embodiment shown in FIGS. 1–3, the second holder member 2 can be detached from the pedestal 5 by pulling the support 6 in vertical direction, together with the holder member 2, out of the pedestal 5. The connection between the support 6 and the pedestal 5 is effected with the aid of a frictional connection formed by one or two rubber rings 11 which are received with a clamped fit between the support 6 and the pedestal 5.

To prevent dust settling on the holder member 1, 2 and the teeth or molars T disposed therein, the present exemplary embodiment includes a transparent bell jar 7 which can be placed over the first and the second holder members 1, 2 and which, in closed position, is in engagement with the pedestal 5. Also for the connection between the bell jar 7 and the pedestal 5, use is made of a flexible ring 12 which is confined with a clamped fit between the inside of the lower edge of the bell jar 7 and a groove 13 in the pedestal 5.

To indicate clearly to which the device in question belongs, the device can include a data plate 8. In the present case, this data plate 8 is mounted on the pedestal 5.

Provided in the pedestal 5 is a chamber 9 for accommodating an information carrier 14, such as, for instance, a "teeth shedding logbook". In such a teeth shedding logbook it can be entered when and which teeth T have fallen off. This teeth shedding logbook can also be designed as an insert sheet folded accordion fashion. In addition to data about lost teeth, other data, such as, for instance, the name and/or a picture of the owner and/or the giver, can be mentioned or represented.

To give the device a still more personal character, it may be provided with a chamber 10 including a window. The chamber 10 is intended for receiving therein a lock of hair of the owner of the device.

Figure 4:
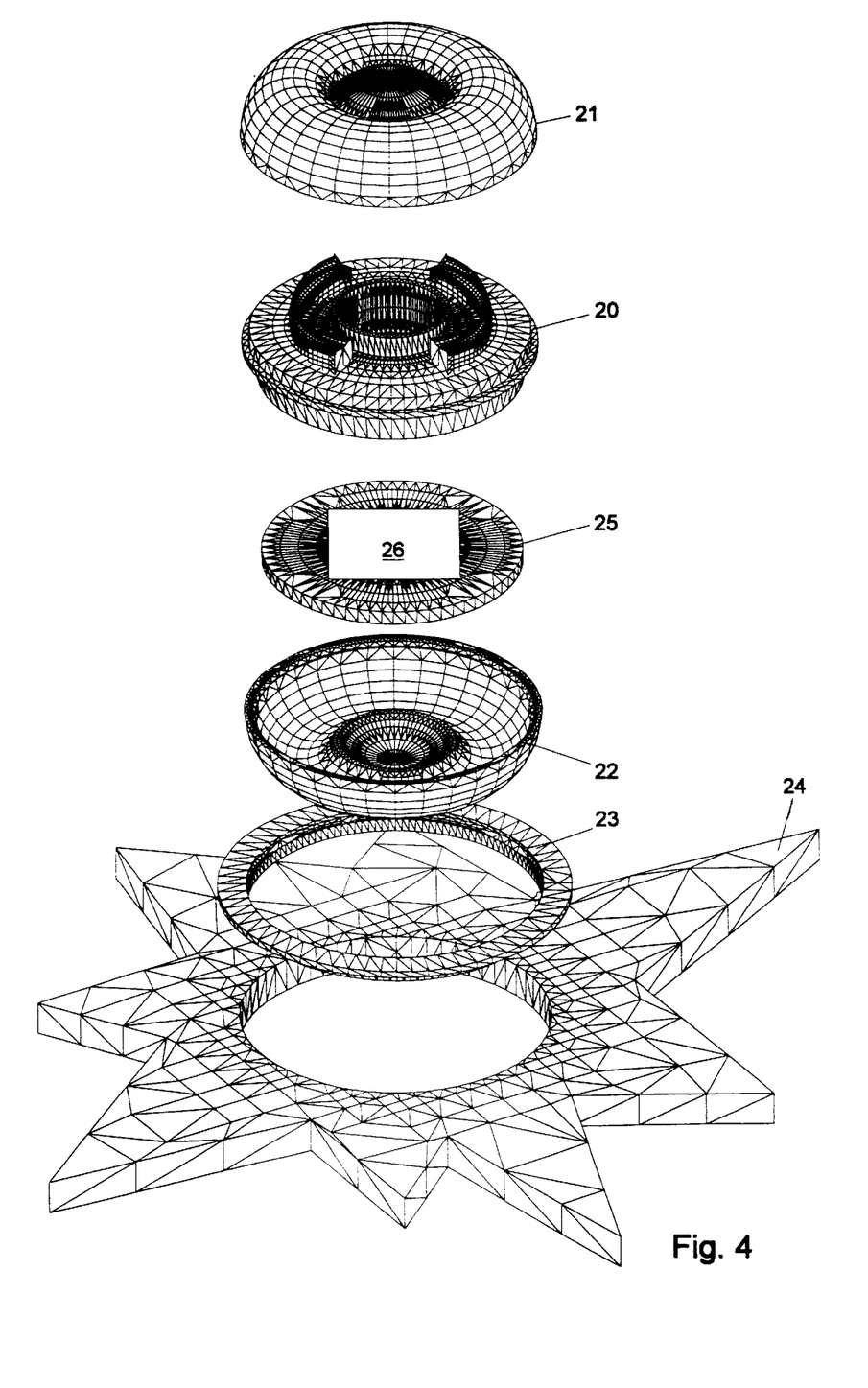
FIG. 4 shows an exploded perspective view of a second exemplary embodiment of a device according to the invention.
Figure 5:
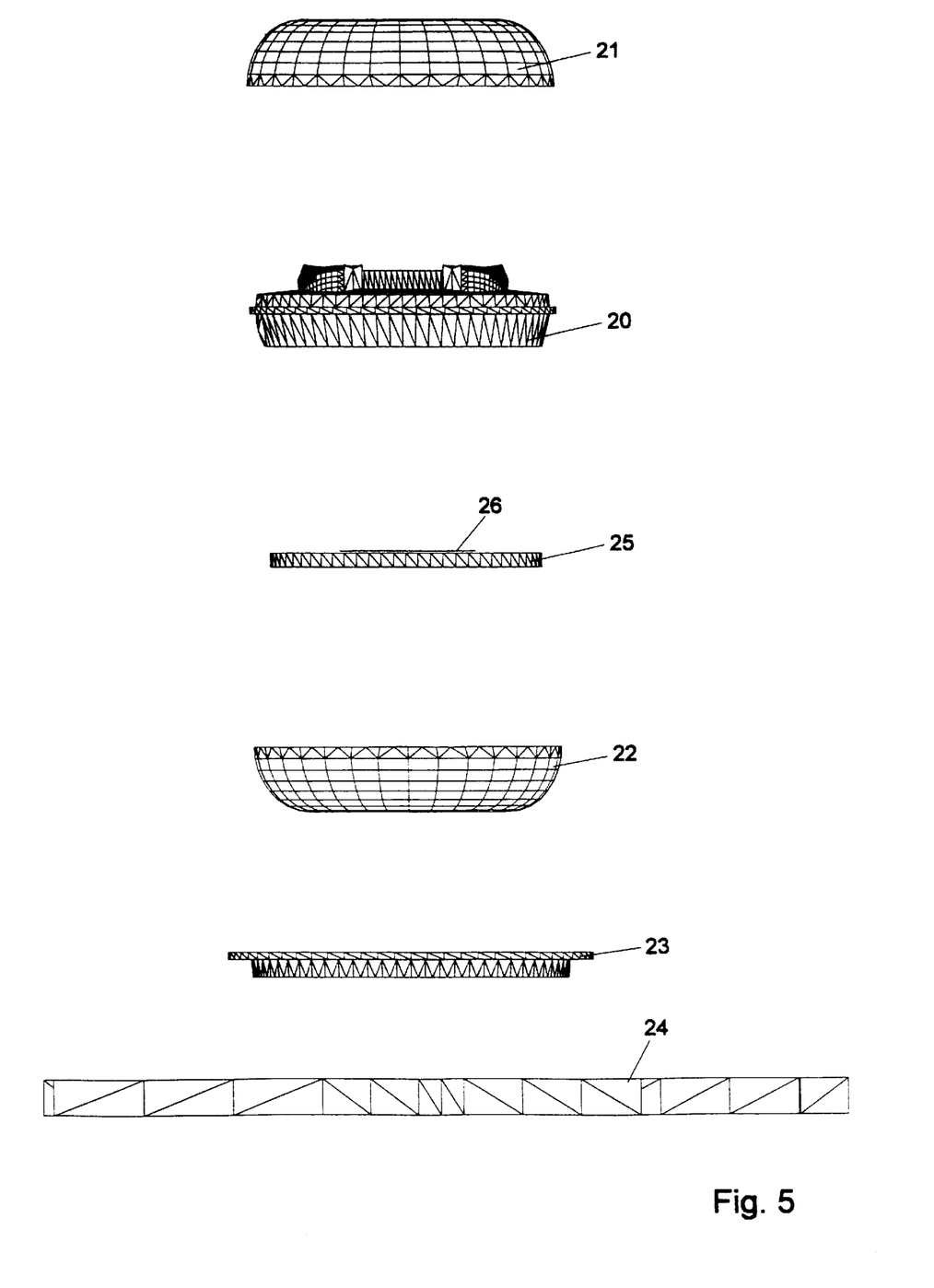
FIG. 5 shows a side elevation of the perspective view represented in FIG. 4.

FIGS. 4 and 5 show, in exploded view, a second exemplary embodiment of a device according to the invention. The second exemplary embodiment comprises a holder member 20, a cover 21 and a bottom 22. Optionally, using a clamping ring 23, a decorative frame 24 can be click-fitted onto the bottom 21, the cover 21 or the holder member 20. In the present exemplary embodiment, the decorative frame 24 is designed as a star. It will be clear that other designs are also possible within the scope of the invention. Preferably, the cover and/or the bottom are of transparent design, so that the holder 20 is visible. Optionally, between the holder 20 and the bottom member 22, a teeth shedding logbook 25 may be provided. The teeth shedding logbook/information booklet can be provided, for instance, with a photograph 26 depicting the owner of the device.

Figure 7:
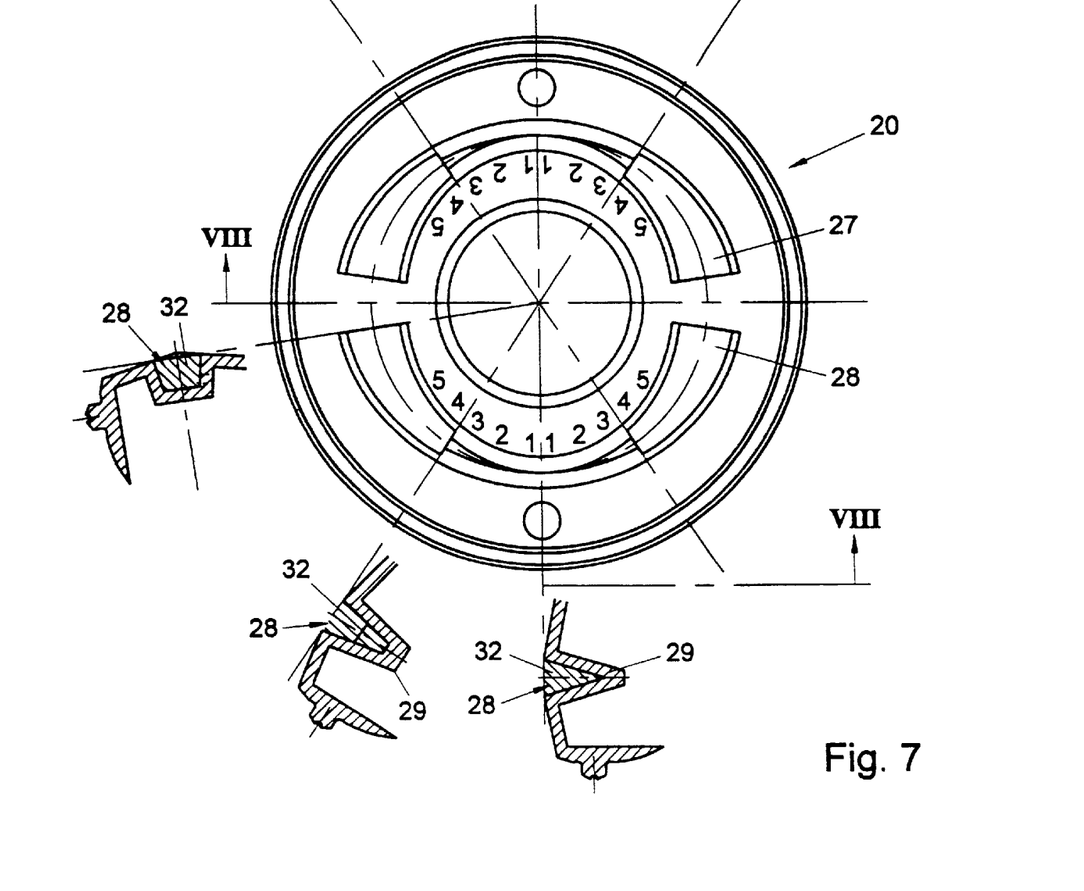
FIG. 7 shows a top plan view of the holder member of the exemplary embodiment represented in FIGS. 4–6.
Figure 8:
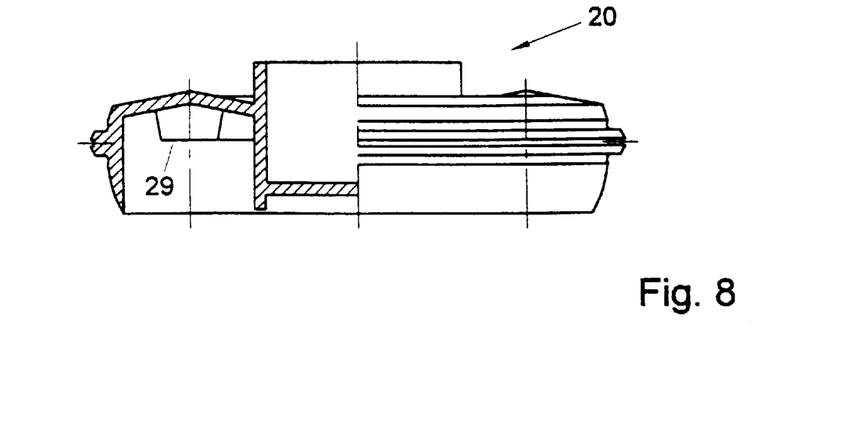
FIG. 8 shows a cross-sectional view and front view of the holder member represented in FIG. 7, taken on the line VIII—VIII in FIG. 7.

The holder member 20 is once more represented clearly in FIGS. 7 and 8. It is clearly visible that the holder member 20 is provided with two receiving grooves 27, 28 accommodating a substance 32 which is plastic at least under certain conditions. The receiving grooves 27, 28 are intended for receiving therein the lost teeth and molars T. It is clear that the width of the receiving grooves 27, 28 varies, so that the receiving grooves 27, 28 adjacent position 1 are suitable in particular for receiving front teeth, while the receiving grooves 27, 28 adjacent the positions 5 are suitable in particular for receiving molars. All this is also clearly indicated in the sectional views represented in FIG. 7. The dimensions of the receiving grooves 27, 28 are such, and the amount of plastic substance that is accommodated in the receiving grooves 27, 28 is such, that the root or the residual portion of the side of the tooth or molar remote from the crown, in mounted condition of the tooth or molar, is substantially completely embedded in the plastic substance, so that a prolonged retention of the tooth or molar in the plastic substance is ensured. In the present exemplary embodiment, the holder member 20 is provided with two receiving grooves 27, 28. It is also possible, however, that a single receiving groove is provided, accommodating both the lower teeth and the upper teeth and molars.

Figure 6:
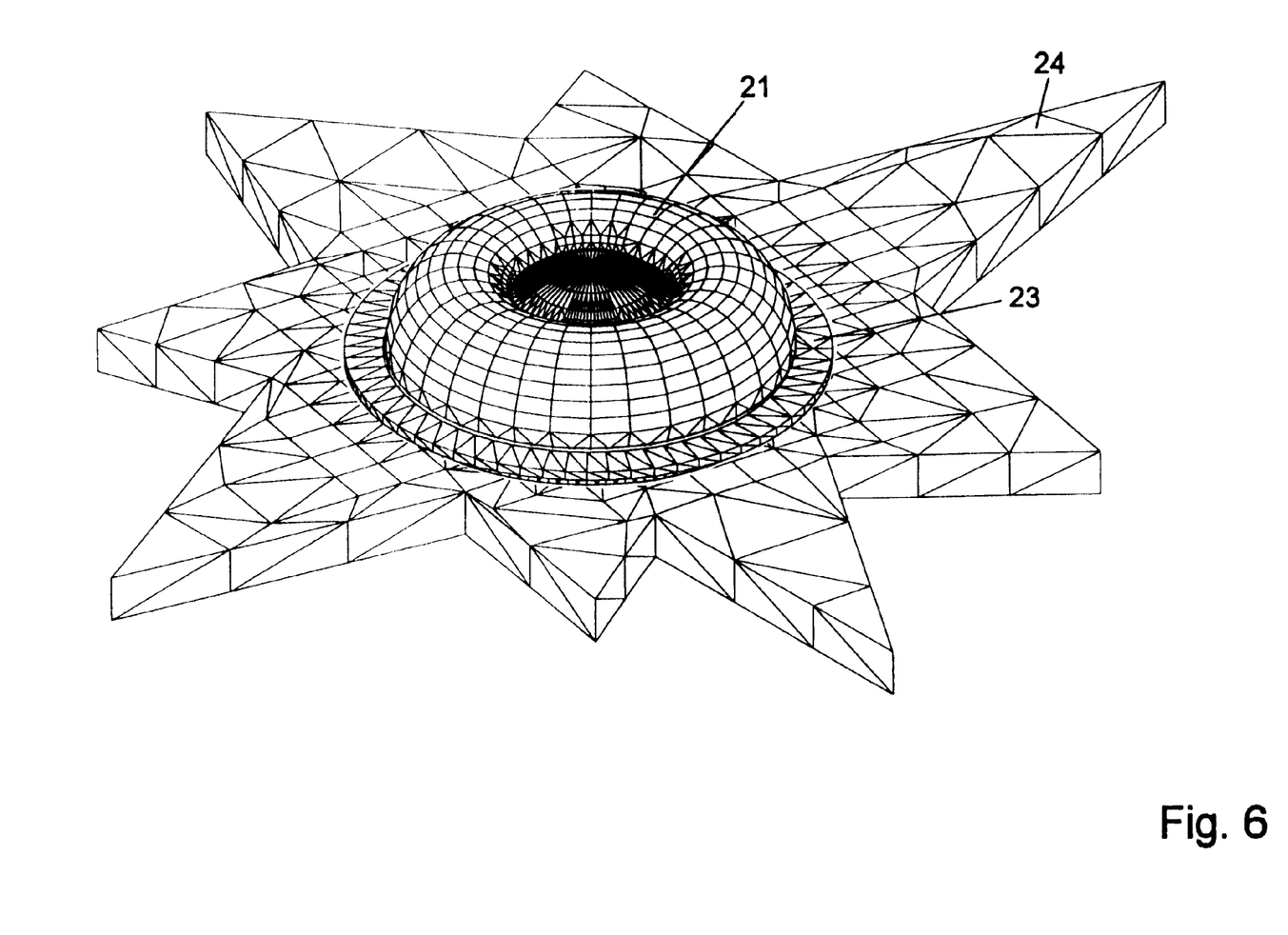
FIG. 6 shows the exemplary embodiment of FIGS. 4 and 5 in assembled condition.

FIG. 8 shows the holder member 20, partly in cross section and partly in side elevation. The groove 28 is bounded by a wall portion 29 which is clearly visible in FIG. 6.

Figures 9, 10:
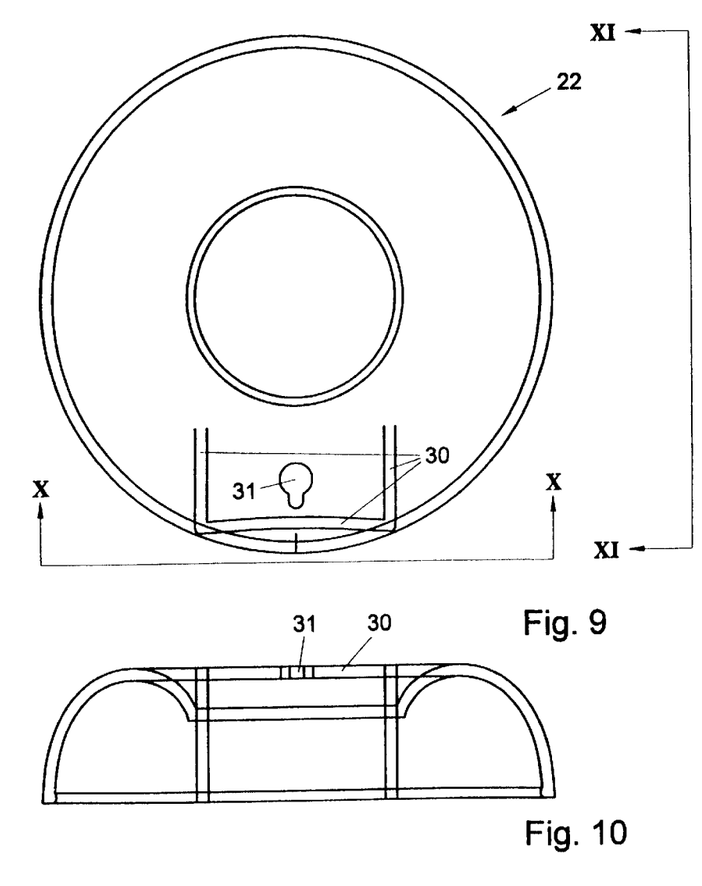
FIG. 9 shows a rear view of an adapted bottom member intended for the exemplary embodiment represented in FIGS. 4–6.
FIG. 10 shows a side elevation of the bottom member represented in FIG. 9, from the direction X—X.
Figure 11:
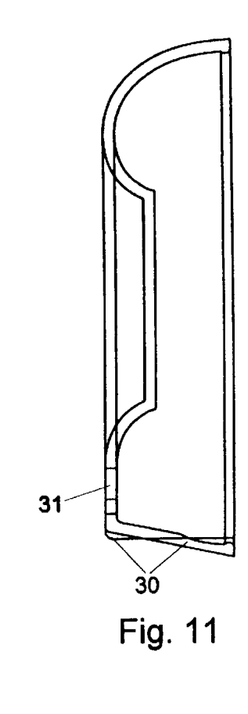
FIG. 11 shows a side elevation of the bottom member represented in FIG. 9, from the direction of XI—XI.

FIGS. 9–11 show, respectively, a rear view and two side elevations of an alternative embodiment of the bottom member 22. This bottom member 22 differs from the bottom member represented in FIGS. 4 and 5 in that it is provided with a support 30, integrally connected with the bottom member, by means of which the device can be arranged on a horizontal surface at a slight indication or in vertical position. Optionally, the support 30 may be provided with a suspension eye 31 by which the device can be suspended from the wall. It will be clear that when use is made of the support 30, a decorative frame as represented in FIGS. 4 and 5 is not possible anymore. It is noted that the decorative frame may at the same time be designed as support, so that the device can be arranged vertically or at an inclination on a horizontal surface. When the device is suspended by the suspension eye 31, such a decorative frame can be present.

The end user, for obtaining a prolonged retention of the fallen-off teeth and molars, only needs to press the teeth and molars into the plastic substance, such that the root or the residual portion of the side of the tooth or molar remote from the crown is substantially completely embedded in the plastic, thereby ensuring prolonged retention of the tooth or molar in the plastic substance. Optionally, after all teeth and molars have been placed in the holder member, a curing agent can be applied to the plastically deformable plastic, so that the plastic properties are lost and the prolonged attachment changes from a detachable to a fixed prolonged attachment.

It will be clear that the invention is not limited to the exemplary embodiments described and that various modifications are possible within the scope of the invention.

What is claimed is:

1. A device for displaying deciduous teeth and molars (T), comprising at least one holder member provided with a tooth and molar receiving means, characterized in that the tooth and molar receiving means comprises a substantially U-shaped continuous deformable portion having dimensions being such that the upon pressing the deciduous teeth and molars therein, the root portions of the deciduous teeth and molars (T) will be substantially completely embedded so that a prolonged attachment is ensured, said continuous deformable portion being a synthetic resin which has plastic properties at room temperature and which retains those plastic properties for a prolonged period of time.

2. A device according to claim 1, characterized in that the at least one holder member is provided with at least one recess in which the synthetic resin is received.

3. A device according to claim 2, characterized by a first, continuous, groove-shaped recess (27) for receiving the upper teeth and upper molars, and by a second, continuous groove-shaped recess (28) for receiving the lower teeth and lower molars.

4. A device according to claim 2, characterized by a single holder member (2) in which the at least one recess (27, 28) is further recessed, in which the synthetic resin (32) is received.

5. A device according to claim 4, characterized in that the device comprises a bottom member (22) and a cover member (21) in which the holder member (20) to receivable.

6. A device according to claim 5, characterized in that the bottom member (22) or the cover member (21) comprise means (30) by which the device can be arranged on a horizontal surface in upright position or in an inclined position.

7. A device according to claim 5, characterized in that the bottom member (22) comprises means (31) for suspending the device.

8. A device according to claim 5, characterized by a clamping ring (23) and a decorative frame (24) which is mountable on the device using the clamping ring (23).

9. A device according to claim 2, characterized by a single, continuous, groove-shaped recess for receiving both the upper teeth and molars and the lower teeth and molars.

10. A device according to claim 9, characterized in that it comprises a transparent bell jar (7) which is placeable over the first and the second holder member (1, 2) and in a closed position is in engagement with the pedestal (5).

11. A device according to claim 1, characterized in that the synthetic resin continues to exhibit substantially the same plasticity up to a temperature of at least about 65° C.

12. A device according to claim 1, characterized in that it comprises a first holder member and a second holder member, the first holder member (1) being connected with a pedestal (5), and the second holder member (2) being provided with a support which is detachably connected to the pedestal (5).

13. A device according to claim 9, characterized in that it comprises a transparent bell jar (7) which is placeable over the first and the second holder member (1, 2) and in a closed position is in engagement with the pedestal (5).

14. A device according to claim 1, characterized by a data plate (8) which is mounted on the device.

15. A device according to claim 1, characterized by a chamber (9) for receiving therein an information carrier.

16. A device according to claim 1, characterized in that the device comprises a chamber (10) which is provided with a window, the chamber (10) being intended for receiving therein a lock of hair.

17. A device according to claim 1, characterized by a holder member in which, for forming the deformable portion, at least one elastically deformable clamping groove is incorporated.

18. A method for displaying deciduous teeth and molars in a holder member (1, 2; 20), the holder member (1, 2; 20) comprising at least one substantially U-shaped continuous recess (27, 28) in which a synthetic resin which has plastic properties at room temperature and which retains those plastic properties for a prolonged period of time (3, 4; 32) is provided, the dimensions of the at least one recess (27, 28) and the amount of synthetic resin (3, 4; 32) provided therein being such that upon pressing the deciduous teeth or molars (T) therein, the root portions of the teeth and molars are substantially completely embedded in the synthetic resin so that a prolonged attachment is ensured.

19. A method according to claim 18, characterized in that, after all the teeth and molars (T) have been placed in the holder member (1, 2; 20), a curing agent is applied to the synthetic resin (3, 4; 32), such that the plastic properties are lost and the prolonged attachment changes from a detachable to a fixed prolonged attachment.

* * * * *